United States Patent
Sedun et al.

(10) Patent No.: US 6,972,273 B2
(45) Date of Patent: Dec. 6, 2005

(54) COMPOSITION AND METHOD FOR SELECTIVE HERBICIDE

(75) Inventors: Frederick S. Sedun, North Saanich (CA); Kim F. Taylor, Shawnigan Lake (CA); Cameron D. Wilson, British Columbia (CA); Diana L. Parker, Brentwood Bay (CA); David S. Almond, Victoria (CA)

(73) Assignee: W. Neudorff GmbH KG, Emmerthal (DE)

( * ) Notice: Subject to any disclaimer, the term of this patent is extended or adjusted under 35 U.S.C. 154(b) by 0 days.

(21) Appl. No.: 10/374,643

(22) Filed: Feb. 26, 2003

(65) Prior Publication Data

US 2003/0181332 A1 Sep. 25, 2003

Related U.S. Application Data

(60) Provisional application No. 60/361,217, filed on Mar. 1, 2002.

(51) Int. Cl.⁷ .......................... A01N 47/36; A01N 59/00
(52) U.S. Cl. ..................... 504/212; 504/124; 504/125; 504/213; 504/214; 504/215; 504/121; 504/113; 504/361
(58) Field of Search ................. 504/212, 124, 504/125, 213, 214, 215, 121, 113, 361, 116, 364; 424/405

(56) References Cited

U.S. PATENT DOCUMENTS

| | | | | |
|---|---|---|---|---|
| 5,500,130 A | * | 3/1996 | Smith et al. ................. 210/703 |
| 5,520,818 A | * | 5/1996 | Smith et al. ................. 210/703 |
| 5,585,005 A | * | 12/1996 | Smith et al. ................. 210/703 |
| 5,656,571 A | * | 8/1997 | Miller et al. ................ 504/361 |
| 5,668,082 A | * | 9/1997 | Miller et al. ................ 504/113 |
| 6,107,246 A | * | 8/2000 | Prescott ....................... 504/116 |
| 6,117,823 A | | 9/2000 | Smiley |
| 6,258,749 B1 | * | 7/2001 | Nonomura ................... 504/121 |
| 6,258,750 B1 | | 7/2001 | Simpson et al. |
| 6,271,177 B1 | | 8/2001 | Hudetz |
| 6,323,153 B1 | | 11/2001 | Smiley |
| 6,383,985 B1 | | 5/2002 | Sedun et al. |
| 6,426,093 B1 | * | 7/2002 | Chevion et al. ............. 424/638 |
| 6,455,472 B1 | * | 9/2002 | Fischer et al. ............... 504/138 |
| 6,541,422 B2 | * | 4/2003 | Scher et al. .................. 504/116 |
| 6,589,912 B2 | * | 7/2003 | Kawai .......................... 504/120 |
| 6,706,666 B2 | * | 3/2004 | Hasebe et al. ............... 504/365 |
| 2002/0016491 A1 | | 2/2002 | Scher et al. |

FOREIGN PATENT DOCUMENTS

| | | |
|---|---|---|
| DD | 260646 | 10/1988 |
| DD | 295077 | 10/1991 |
| JP | 58162508 | 9/1983 |
| JP | 7-215806 | 8/1995 |
| WO | 0144236 | 6/2001 |

* cited by examiner

*Primary Examiner*—Sabiha N. Qazi
(74) *Attorney, Agent, or Firm*—Nutter, McClennen & Fish LLP

(57) ABSTRACT

An environmentally safe selective herbicide is provided that includes at least one metal component and at least one chelating agent. The metal component can have a variety of forms, but is preferably in the form of a metal salt, a metal chelate, or combinations thereof. The chelating agent can also have a variety of forms, but is preferably in the form of a metal chelate, a salt, an acid, or combinations thereof. Methods of use are also provided.

15 Claims, No Drawings

COMPOSITION AND METHOD FOR SELECTIVE HERBICIDE

CROSS-REFERENCE TO RELATED APPLICATIONS

This application claims priority from U.S. Provisional Patent Application Ser. No. 60/361,217, filed on Mar. 1, 2002, entitled "Composition and Method for Selective Herbicide," which is expressly incorporated by reference herein.

FIELD OF THE INVENTION

The present invention relates to selective herbicide compositions and methods for controlling unwanted vegetation.

BACKGROUND OF THE INVENTION

The selective control of unwanted vegetation, such as, for example, weeds, is a major industry. Vegetation can be controlled using herbicides that are non-selective or selective, and systemic or contact. Non-selective herbicides kill or damage all plants to which they are applied, i.e., both desired and undesired vegetation. In contrast, selective herbicides eliminate or inhibit the growth of unwanted vegetation, while leaving the desired vegetation relatively unharmed. Contact herbicides are applied to the top growth, or portion(s) of the plant located above the soil surface. These herbicides, which kill or damage the top-growth only, are typically effective on annual weeds or vegetation. In contrast, systemic herbicides are initially taken up by the roots and/or the foliage of the plant and subsequently translocated to tissues that are remotely located from the point of application.

At present, there are several common types of selective herbicides on the market. The Phenoxy Acid-Type selective herbicides include 2,4-D (2,4-Dicholorophenoxyacetic acid), 2,4-DP (2,4-Dicholorophenoxypro or Dichlorprop), and mecoprop (2-(2-methyl-4-chlorophenoxy)propionic acid). These systemic selective herbicides are initially taken up by the leaves, stem or roots of a plant, and subsequently moved throughout the plant. 2,4-D and 2,4-DP stimulate nucleic acid and protein synthesis and affect enzyme activity, respiration, and cell division, while mecoprop affects enzyme activity and plant growth. The Benzoic Acid-Type selective herbicides include dicamba, another systemic selective herbicide that is initially taken up by the leaves and roots of a plant and subsequently moved throughout the plant. Benzoic Acid-Type selective herbicides are similar to the Phenoxy Acid-Type selective herbicides described above.

Currently, these selective herbicides present major toxicological and environmental concerns. Attempts have been made to create selective herbicides that are effective, yet environmentally safe. Smiley (U.S. Pat. No. 6,323,153) teaches using various salts of chelating agents that are capable of forming stable coordination complexes with calcium and magnesium salts to control the growth of various weeds in lawns. In another patent (U.S. Pat. No. 6,117,823), Smiley discloses the use of aliphatic carboxylic acid diesters, such as dimethyl succinate and dimethyl glutarate, as non-selective herbicides. Simpson (U.S. Pat. No. 6,258,750) teaches an algaecide, herbicidal and/or fungicidal composition including a metal, the chelating agent, ethylene diamine disuccinic acid (EDDS) or a salt thereof, and a source of calcium and chloride ions. Hudetz (U.S. Pat. No. 6,271,177) teaches a herbicide that combines a sulfonyl urea compound and a water-soluble iron compound, while Sedun (WO 01/50862) discloses a herbicidal composition containing a combination of maleic hydrazide (MH) and carboxylic acids. Sedun also discloses that MH may be combined with an amine salt of a carboxylic acid (e.g., triethanolamine salts), which is chemically distinct from compounds that include amine and carboxylic function groups on the same molecule (e.g., EDTA).

Thus, there is presently a need for safer alternatives to currently used selective herbicides. There also exists a need for an environmentally safe selective herbicide that can selectively control unwanted plants, grasses and weeds, while leaving other plants and crops relatively unharmed.

SUMMARY OF THE INVENTION

The present invention is directed to an environmentally safe selective herbicide that includes at least one metal component and at least one chelating agent. The metal component can have a variety of forms, but is preferably in the form of a metal salt, a metal chelate, or combinations thereof. The chelating agent can also have a variety of forms, but is preferably in the form of a metal chelate, a salt, an acid, or combinations thereof. Methods of use are also provided.

The disclosed herbicidal compositions can be made as a ready-to-use composition, a liquid concentrate, or a dry concentrate. Plants such as lawn grasses remain relatively undamaged by the disclosed compositions, whereas unwanted plants such as dandelions (*Taraxacum officinale*), daisies (*Bellis perennis*), chickweed (*Stellaria media*), mosses, liverworts, algae are severely damaged or killed by the disclosed compositions.

Unless otherwise noted, all percentages referred to herein are percent by weight.

DETAILED DESCRIPTION OF THE INVENTION

The present invention provides an environmentally compatible, selective herbicidal composition comprising a combination of a metal component and a chelating agent. The metal component of the formulation can be in the form of a metal salt, a metal chelate, or combinations thereof, and the chelating agent can be in the form of a metal chelate, a salt, an acid, or combinations thereof.

The metal component of the present invention can include a variety of metals, but preferably includes a transition metal ion. Suitable transition metal ions include, for example, copper ions, iron ions, manganese ions, nickel ions, zinc ions, and combinations thereof. In an exemplary embodiment, the metal component includes an iron ion. The metal ions can be added in a variety of ionic states. By way of non-limiting example, iron ions used in the present invention can be added as either $Fe^{+2}$ ions, $Fe^{+3}$ ions, and mixtures thereof.

The metal component of the present invention can also be added in a variety of forms. In one embodiment, the metal ions can be added as a metal salt. Preferably, when the metal ions are added as a salt, they are added as metal chlorides, metal sulfates, metal nitrates, metal citrates, metal phosphates, metal chelates, metal sulfides, metal sulfites, metal succinates, metal gluconates, metal lactates, metal formates, metal nitrites, metal salicylates, metal carboxylic acids, and in combinations of these salts.

In another embodiment, the metal ions can be added to the herbicidal composition as a metal chelate. A variety of chelating agents can be used in the selective herbicide compositions of the present invention to form a metal chelate. By way of non-limiting example, suitable chelating agents include aconitic acid, alanine diacetic acid (ADA), alkoyl ethylene diamine triacetic acids (e.g., lauroyl ethylene diamine triacetic acids (LED3A)), aminotri (methylenephosphonic acid) (ATMP), asparticaciddiacetic acid (ASDA), asparticacidmonoacetic acid, diamino cyclohexane tetraacetic acid (CDTA), citraconic acid, citric acid, 1,2-diaminopropanetetraacetic acid (DPTA-OH), 1,3-diamino-2-propanoltetraacetic acid (DTPA), diethanolamine, diethanol glycine (DEG), diethylenetriaminepentaacetic acid (DTPA), diethylene triamine pentamethylene phosphonic acid (DTPMP), diglycolic acid, dipicolinic acid (DPA), ethanolaminediacetic acid, ethanoldiglycine (EDG), ethionine, ethylenediamine (EDA), ethylenediaminediglutaric acid (EDDG), ethylenediaminedi (hydroxyphenylacetic acid (EDDHA), ethylenediaminedipropionic acid (EDDP), ethylenediaminedisuccinate (EDDS), ethylenediaminemonosuccinic acid (EDMS), ethylenediaminetetraacetic acid (EDTA), ethylenediaminetetrapropionic acid (EDTP), ethyleneglycolaminoethylestertetraacetic acid (EGTA), gallic acid, glucoheptonic acid, gluconic acid, glutamicaciddiacetic acid (GLDA), glutaric acid, glyceryliminodiacetic acid, glycinamidedisuccinic acid (GADS), glycoletherdiaminetetraacetic acid (GEDTA), 2-hydroxyethyldiacetic acid, hydroxyethylenediaminetriacetic acid (HEDTA), hydroxyethyldiphosphonic acid (HEDP), 2-hydroxyethyl imino diacetic acid (HIMDA), hydroxyiminodiacetic acid (HIDA), 2-hydroxy propylene diamine disuccinic acid (HPDDS), iminodiacetic acid (IDA), iminodisuccinic acid (IDS), itaconic acid, lauroyl ethylene diamine triacetic acids (LED3A), malic acid, malonic acid, methylglycinediacetate (MGDA), methyliminodiacetic acid (MIDA), monoethanolamine, nitrilotriacetic acid (NTA), nitrilotripropionic acid (NPA), N-phosphonomethyl glycine (glyphosate), propyldiamine tetraacetic acid (PDTA), salicylic acid, serinediacetic acid (SDA), sorbic acid, succinic acid, sugars, tartaric acid, tartronic acid, triethanolamine, triethylenetetraamine, triethylene tetraamine hexaacetic acid (TTHA), and combinations thereof. In an exemplary embodiment, the chelating agent is EDTA, HEDTA, EDG, EDDS, GLDA MGDA, isomers thereof, and combinations thereof.

Other suitable chelating agents include aminopolycarboxylic acid, amines, amides, phosphonic acid and combinations thereof. Amino acids can also be used as chelating agents in the present invention. Suitable amino acids include alanine, arginine, asparagine, aspartic acid, glutamic acid, glutamine, glycine, histidine, isoleucine, leucine, lysine, methionine, proline, serine, threonine, tyrosine, valine, and combinations thereof.

Other suitable chelating agents that can be used in the herbicidal compositions of the present invention include beet molasses, carboxylic acids and the salts thereof, salicylic acid and salts thereof, such as ammonium salicylate, citric acid, and combinations thereof.

The chelating agent of the present invention can also be added to the herbicidal composition in a variety of forms, alone, or in combination. In one embodiment, it can be a free acid. In another embodiment the chelating agent can be a salt. Preferably, in this embodiment, the chelating agent is added as a sodium salt, potassium salt, calcium salt, ammonium salt, amine salt, amide salt, and combinations thereof. In another embodiment, the chelating agent can be added as an alkali metal chelate, including calcium and magnesium. Other suitable metal chelates are described above with respect to the metal component.

The end-use concentration of these ingredients of the herbicidal compositions of the present invention can vary depending on the form of the metal component and the chelating agent. When referring to the amount, e.g., concentration and molar ratio, of the metal component in the composition, the amount is based on the amount of metal ions present within the metal component.

Where the selective herbicide composition includes a metal salt and a chelating agent, the concentration of the metal ion and the chelating agent can vary significantly. By way of non-limiting example, the concentration of metal applied to the plant can be in the range of about 0.01 and 5% by weight, and more preferably about 0.05 to 2% by weight, while the concentration of the chelating agent applied to the plant can be in the range of about 0.1 to 10% by weight, and more preferably about 0.2 to 5% by weight. The molar concentration of each ingredient can also vary. Thus, the molar ratio of metal to chelating agent can be substantially equal to one, greater than one, substantially greater than one, less than one, or substantially less than one. More preferably, the molar ratio of metal to chelating agent is in the range of about 0.05:1 to 20:1, and more preferably is about 0.2:1 to 5:1.

Where the composition includes a metal salt and a metal chelate, on the other hand, the metal is preferably present at a molar amount greater than the amount of chelating agent. In an exemplary embodiment, the concentration of metal ions applied to the plant is preferably in the range of about 0.01 to 5.0% by weight, and more preferably about 0.05 to 2.0% by weight, while the concentration of chelating agent(s) applied to the plant is about 0.1 to 10.0% by weight, and more preferably between 0.2 to 5.0% by weight. The molar concentration of each ingredient can also vary. Preferably, the molar ratio of metal to chelating agent is in the range of about 1.0:0.05 to 1.0:1.0, and more preferably is about 1.0:0.1 to 1.0:1.0.

In another embodiment, the composition can include a metal chelate and a chelating agent. While the amount can vary, in this embodiment the chelating agent is present at an amount greater than an amount of metal. In an exemplary embodiment, the concentration of metal applied to the plant is preferably in the range of about 0.01 to 5.0% by weight, and more preferably about 0.05 to 2.0% by weight, while the concentration of the chelating agent applied to the plant is about 0.1 to 10.0% by weight, and more preferably between 0.2 to 5.0% by weight. In yet another embodiment, the composition can include one or more metal chelates. While the amount can vary, the concentration of metal applied to the plant is preferably in the range of about 0.1 to 5.0% by weight, and more preferably about 0.1 to 2.0% by weight.

Besides the above ingredients, a variety of other components can be added to the selective herbicide compositions. By way of non-limiting example, these additives can include fertilizers, growth regulators, amino acids, additional herbicides, thickening agents, dyes and combinations thereof.

A variety of fertilizers may be added to the herbicidal composition of the present invention. Preferably, the fertilizer is a nitrogen-containing fertilizer that is effective to promote the rapid growth of grass, thereby allowing the grass to shade and out-compete the damaged weeds. The end-use concentration of added fertilizer(s) can vary, but preferably, the concentration of fertilizer is in the range of about 0.1 to 5% by weight.

A variety of growth regulators may also be added to the herbicidal composition of the present invention. By way of non-limiting example, the growth regulators added to the herbicidal compositions can include maleic hydrazide (MH), cycocel (2-chloroethyl-trimethyl ammonium chloride), auxins, and combinations thereof. The end-use concentration of the additional growth regulators can vary, but preferably, the concentration is between about 100 ppm and 2% by weight.

The herbicidal compositions of the present invention can also include natural growth regulators, such as for example, salicylic acid, salts of salicylic acid including ammonium salicylate, jasmonates, ethylene, auxins, gibberellins, cytokinins, abscisic acid, and combinations thereof. The end-use concentration of these natural growth regulators can vary, but preferably, the concentration is between about 10 ppm and 5% by weight.

In addition to the selective herbicides disclosed herein, the herbicidal compositions of the present invention can include other herbicides as a co-active ingredient. The co-active ingredients that can be added as additional herbicides include glyphosate, glufosinate, fatty acids and salts thereof, urea, sodium, borax, copper sulfate, carboxylic acids and the salts thereof, ammonium salts, and combinations thereof. The end-use concentration of the additional herbicide(s) can vary, but preferably, the concentration is in the range of about 100 ppm to 5% by weight.

Furthermore, a variety of thickening agents may be added to the herbicidal compositions disclosed herein. Preferably, these thickening agents include Rhodopol 23 (Rhone Poulenc), VanGel B (R. T. Vanderbilt), Kelzan S (Merck & Co.), guar gum, propylene glycol, glycerol, and combinations thereof. The end-use concentration of added thickening agent(s) can vary, but preferably, the concentration is in the range of about 0.01 to 1% by weight.

Other additives may be included in the herbicidal compositions disclosed herein. By way of non-limiting example, a herbicidal composition according to the present invention can include humectants, antioxidants, stabilizing agents, wetting agents, herbicide synergists, sequestrants, and combinations thereof. Suitable humectants include, for example, propylene glycol, glycerin, beet molasses, and combinations thereof. Suitable antioxidants include, for example, citric acid, while suitable stabilizing agents include citric acid, ammonium salts, and combinations thereof. Suitable wetting agents include, for example, carboxylic acids and the salts thereof and silicone polymers such as Silwet 77 (Witco Corp, CT, USA). Suitable herbicide synergists and suitable sequestrant additives include, for example, ammonium salts. The end-use concentration of these additives may vary, but preferably, the concentration is between about 0.1 and 5% by weight.

In use, the formulation of the selective herbicide of the present invention can vary. Preferably, the herbicidal compositions are formed as a ready-to-use composition, a liquid concentrate, or a dry concentrate. The solvents used in the ready-to-use liquid composition and liquid concentrate forms can vary. Preferably, the solvent is a poor wetting agent on plant leaves, essentially equal to that of water. Grass leaves are often vertical and hard to wet, whereas many weeds, such as the dandelion, are horizontal and easy to wet. Solutions that are poor wetting agents are advantageous because they tend to bead up and run off of grass leaves, while spreading onto leaves of the horizontal weeds, such as the dandelion. More preferably, the solvent(s) used in the formulation of the disclosed herbicidal compositions are propylene glycol, glycerin, alcohols such as tetrahydrofurfuryl alcohol (THFA) and combinations thereof.

The pH of the herbicidal solution can vary, but preferably, the herbicidal compositions of the present invention are effective over a wide range of pH values. More preferably, the pH of the herbicidal compositions of the present invention is between about 1.5 and 10. After the formulation has been prepared, the pH of the solution can be measured and adjusted as necessary. The pH values can be measured using standard pH meters, with glass bulb electrodes.

A typical ready-to-use (RTU) formulation according to one embodiment of the present invention is FeEDTA RTU with 0.2% iron. The ingredients are as follows:

| Ingredient | Concentration by weight (%) |
| --- | --- |
| Water | 96.75% |
| $Na_4EDTA$ | 1.80% |
| $Fe(NO_3)_3 \cdot 9H_2O$ | 1.45% |

The RTU formulation is prepared by adding water to a vessel, and adding $Na_4EDTA$ the water while stirring. Once dissolved, the ferric nitrate is added, followed by additional stirring to dissolve the ferric nitrate. This solution can then be sprayed onto areas of lawn and dandelion using a band sprayer, at a rate of 100 ml/m$^2$.

The composition of the present invention can be applied to a variety of undesired vegetation in both residential and commercial plant or crop areas. Preferably, the herbicidal compositions are effective to control weeds and unwanted plants, including dicotyledonous plants, monocotyledonous plants, conifers, cycads, ferns, horsetails, mosses, liverworts, and algae. It is very effective against common weeds such as dandelions (*Taraxacum officinale*), daisies (*Bellis perennis*), and chickweed (*Stellaria media*).

The following non-limiting examples serve to further describe the invention. Unless otherwise specified, all of the iron solutions were made using the same molar concentration of iron ion as chelating agent. All of the outside tests were done on areas of mixed grass and dandelions that were at least 2 months old. For the greenhouse tests, dandelions were grown in a commercial greenhouse mix, using supplemental lighting and heating. Each plant was grown in a 2¼ inch pot to a minimum diameter of 20 cm. All of the solutions were sprayed onto the plants at a rate of 100 ml/m². The ferrous sulfate formulations that were used in examples 1, 2, 8 and 9 contained 1% iron (180 mM), 18 mM EDTA, 1% citric acid and 0.5% urea. In all of the examples, the amount of iron is identified in brackets as the percent iron on a weight basis.

Killex® (Green Cross, Ontario, Canada) is a commonly used selective lawn herbicide and was included in several field tests as a standard. Killex contains 2,4-D (9.5%), mecoprop (5%) and dicamba (0.9%). The product was diluted 6 ml into 1 L of water solution and applied at rate of 200 Ml/m², as per label instructions.

All plant damage was assessed using a qualitative rating scale from 0 to 9.

| | |
|---|---|
| 0 | No damage |
| 1 | Trace of damage |
| 2 | Trace to slight damage |
| 3 | Slight damage |
| 4 | Slight to moderate damage |
| 5 | Moderate damage |
| 6 | Moderate to severe damage |
| 7 | Severe damage |
| 8 | Very severe damage |
| 9 | Plant dead |

A damage rating of "4" or higher may be high enough to control undesired plants.

EXAMPLE 1

Field Dandelion and Turf Test of Iron Chelates

All of the iron chelates were sprayed once at 0.2% $Fe^{+3}$ (35.8 mM), at a volume of 100 ml/m² onto 0.5 m² areas of mixed grass and dandelions. The spraying of the test was followed by 2 days of rain-free weather. Observations were made 5 days after spraying.

| | pH | Grass Damage (0 to 9) | Dandelion Damage (0 to 9) |
|---|---|---|---|
| FeEDDS (0.2% $Fe^{+3}$) | 7.5 | 3 | 4.5 |
| FeEDTA (0.2% $Fe^{+3}$) | 7.5 | 1 | 8.3 |
| FeHEDTA (0.2% $Fe^{+3}$) | 7.5 | 0 | 8.9 |
| $FeSO_4$ (1% $Fe^{+2}$) | 2.5 | 7 | 6.3 |
| Untreated | | 0 | 0.0 |

EXAMPLE 2

Field Grass and Dandelion Test of FeEDDS and FeHEDTA at pH 3 and 7

The FeEDDS and FeHEDTA solutions contained 0.2% $Fe^{+3}$ (35.8 mM). The ferrous sulfate contained 1% $Fe^{+2}$ (179.1 mM). The solutions were sprayed at a rate of 0.1 L/m² onto 2 plots of 0.5 m² of mixed grass and dandelions. Observations were made 4 days after spraying.

| | pH | Grass Damage (0 to 9) | Dandelion Damage (0 to 9) |
|---|---|---|---|
| FeEDDS (0.2% $Fe^{+3}$) | 3.0 | 2.0 | 5.5 |
| FeEDDS (0.2% $Fe^{+3}$) | 7.0 | 1.0 | 4.0 |
| FeHEDTA (0.2% $Fe^{+3}$) | 3.0 | 0.0 | 7.0 |
| FeHEDTA (0.2% $Fe^{+3}$) | 7.1 | 1.0 | 7.5 |
| $FeSO_4$ (1% $Fe^{+2}$) | 2.6 | 7.0 | 7.0 |
| Untreated | | 0.0 | 0.0 |

EXAMPLE 3

Combinations of FeSO4, EDTA, EDDS and MH, at pH 6 and 3, on Dandelions and Grass This test investigated the effect of 10% chelation and pH on potted grass and dandelions. All of the solutions contained 10% ferrous sulfate heptahydrate, resulting in a $Fe^{+2}$ concentration of 2% (358.1 mM). EDTA and EDDS were added at $1/10^{th}$ of the iron molar concentration (35.8 mM). MH was added 1%. The dandelions and turf grasses were sow in separate pots 3 weeks prior to the start of the test.

The plants were re-sprayed after 9 days.

| | | Plant Damage (0 to 9) | | Plant Death (%) | |
|---|---|---|---|---|---|
| 3 Days After Second Spray | pH | Grass | Dandelion | Grass | Dandelion |
| $FeSO_4$ (2% $Fe^{+2}$) | 6 | 0 | 6.0 | 0 | 17 |
| $FeSO_4$ + MH (0.2% Fe) | 6 | 0 | 7.0 | 0 | 30 |
| $FeSO_4$ + EDTA (0.2% Fe) | 6 | 0 | 8.3 | 0 | 87 |
| $FeSO_4$ + EDDS (0.2% Fe) | 6 | 0 | 7.3 | 0 | 69 |
| $FeSO_4$ + MH + EDTA (0.2% Fe) | 6 | 0 | 8.5 | 0 | 89 |
| $FeSO_4$ + MH + EDDS (0.2% Fe) | 6 | 4 | 7.0 | 0 | 56 |
| $FeSO_4$ (0.2% Fe) | 3 | 4 | 8.2 | 0 | 76 |
| $FeSO_4$ + EDTA (0.2% Fe) | 3 | 1 | 9.0 | 0 | 100 |
| $FeSO_4$ + EDDS (0.2% Fe) | 3 | 0 | 8.7 | 0 | 90 |
| Untreated | n/a | 0.0 | 0 | 0 | 0 |

EXAMPLE 4

Effect of pH on FeHEDTA Applied to Greenhouse Dandelions

This test compared the effects of FeHEDTA at a range of pH values to potted, greenhouse-grown dandelions. All of the solutions were applied at 0.2% $Fe^{+3}$ (35.8 mM). Ammonium sulfate was added at 2%. The plants were re-sprayed after 8 days.

| | Plant Damage (0 to 9) | Dead (#/10) |
|---|---|---|
| Days After Spraying | 7 | 8 + 5 | 8 + 5 |
| FeHEDTA pH 3 (0.2% Fe) | 3.2 | 6.8 | 5 |

-continued

|  | Plant Damage (0 to 9) | Dead (#/10) |  |
|---|---|---|---|
| FeHEDTA pH 5 (0.2% Fe) | 2.6 | 5.4 | 3 |
| FeHEDTA pH 7 (0.2% Fe) | 1.9 | 5.1 | 2 |
| FeHEDTA pH 9 (0.2% Fe) | 2.0 | 3.6 | 1 |
| FeHEDTA pH 11 (0.2% Fe) | 3.8 | 6.6 | 5 |
| FeHEDTA pH 3 + $NH_4SO_4$ (0.2% Fe) | 3.8 | 7.9 | 6 |
| Untreated | 0.0 | 0.0 | 0 |

EXAMPLE 5

Effect of Additives on FeEDDS (0.4% $Fe^{+3}$) on Dandelions

The literature identifies many compounds that can chelate iron. This test evaluated combinations of these compounds with EDDS sprayed onto greenhouse grown dandelions. Maleic hydrazide (MH) was included to investigate the effect of a growth inhibitor on the response of the plant to iron.

All of the additives, except MH and beet molasses, were applied at the same molar concentration as the iron (71.6 mM). NaEDDS was used at twice the molar concentration of iron (143.3 mM). All of the solutions were adjusted to pH 5.1, except as noted, using sodium carbonate. The plants were re-sprayed 7 days after the first spray.

|  | pH | Plant Damage (0 to 9) |  | Dead or Dying (#/10) |
|---|---|---|---|---|
| Days After Spraying |  | 7 | 7 + 7 | 7 + 7 |
| FeEDDS (0.4% $Fe^{+3}$) (A) | 5.2 | 5.8 | 3.8 | 3 |
| (A) "pH 9" (0.4% $Fe^{+3}$) | 8.7 | 5.9 | 5.6 | 3 |
| (A) + ascorbic acid (0.4% $Fe^{+3}$) | 5.1 | 5.7 | 4.5 | 3 |
| (A) + citrate acid (0.4% $Fe^{+3}$) | 5.5 | 7.7 | 5.6 | 4 |
| (A) + malic acid (0.4% $Fe^{+3}$) | 5.1 | 7.0 | 4.1 | 2 |
| (A) + salicylic acid (0.4% $Fe^{+3}$) | 5.1 | 7.4 | 7.7 | 8 |
| (A) + succinic acid (0.4% $Fe^{+3}$) | 5.3 | 6.5 | 5.3 | 1 |
| (A) + tartaric acid (0.4% $Fe^{+3}$) | 5.1 | 7.3 | 5.2 | 4 |
| (A) + $NH_4SO_4$ (0.4% $Fe^{+3}$) | 5.2 | 4.9 | 5.2 | 4 |
| (A) + beet molasses 4% (0.4% $Fe^{+3}$) | 5.2 | 7.1 | 7.5 | 6 |
| (A) + MH 0.2% (0.4% $Fe^{+3}$) | 5.2 | 7.1 | 7.0 | 6 |
| (A) + MH 0.5% (0.4% $Fe^{+3}$) | 5.2 | 7.2 | 8.3 | 8 |

EXAMPLE 6

Effect of Various Fe Chelates on Dandelion Phytotoxicity

This test compared EDG (ethanol diglycine) and EDDS at 0.4% Fe+3 (71.6 mM), with HEDTA 0.2% Fe+3 (35.8 mM). FeEDDS and FeEDG were made with 100% excess chelating agent. FeHEDTA was made with 10% excess chelating agent. The solutions were sprayed onto greenhouse grown dandelions. The plants were resprayed after 7 days.

|  | pH | Plant Damage (0 to 9) |  | Dead Plants (#/10) |
|---|---|---|---|---|
| Days After Spraying |  | 7 | 7 + 5 | 7 + 5 |
| FeEDG (0.4% $Fe^{+3}$) | 8.3 | 1.4 | 6.4 | 1 |
| FeEDDS (0.4% $Fe^{+3}$) | 5.5 | 5.0 | 8.6 | 8 |
| FeHEDTA (0.2% $Fe^{+3}$) | 5.5 | 1.3 | 8.1 | 3 |
| Untreated |  | 0.0 | 0.0 | 0 |

EXAMPLE 7

Potassium Nonanoate KC9 with FeHEDTA on Greenhouse Dandelions

This test compared the damaged caused by combinations of fatty acid and FeHEDTA. FeHEDTA was used at a concentration to 35.8 mM. The treatment with 0.1% Fe contained twice the molar amount of chelating agent as iron. The treatment with 0.2% iron contained the same molar amount of chelating agent as iron Potassium nonanoate (KC9) was used at 0.84%. The plants were re-sprayed 8 days after the first spray.

|  | [$Fe^{+3}$] (mM) | [HEDTA] (mM) | pH | Plant Damage (0 to 9) |  | Dead Plants (#/10) |
|---|---|---|---|---|---|---|
| Days After Spraying |  |  |  | 7 | 8 + 5 | 8 + 5 |
| KC9 | 0.0 | 0.0 | 7.7 | 0.0 | 0.6 | 0 |
| KC9 + FeHEDTA (0.1% $Fe^{+3}$) | 18.0 | 35.8 | 7.8 | 8.1 | 9.0 | 10 |
| KC9 + FeHEDTA (0.2% $Fe^{+3}$) | 35.8 | 35.8 | 7.8 | 5.9 | 7.6 | 7 |
| $FeSO_4$ (0.2% $Fe^{+2}$) | 35.8 | 0.0 | 2.4 | 0.8 | 0.2 | 0 |
| $FeSO_4$ (1% $Fe^{+2}$) | 179.1 | 0.0 | 2.1 | 4.4 | 7.2 | 5 |
| $FeSO_4$ (2% $Fe^{+2}$) | 358.1 | 0.0 | 1.9 | 6.2 | 8.4 | 8 |
| Untreated |  |  |  | 0.0 | 0.0 | 0 |

EXAMPLE 8

Field Daisy Test of Iron Solutions with Added EDTA and Propylene Glycol

Field areas with 10 cm to 20 cm areas of daisy plants (*Bellis perennis* BELPE) were sprayed with various 2% $Fe^{+2}$ iron (358 mM) solutions at a rate of 0.5 L/m$^2$. The areas were assessed 6 days after spraying.

|  | pH | Daisy Mortality (%) |
|---|---|---|
| $FeSO_4$ (2% $Fe^{+2}$) | 2.2 | 6 |
| $FeSO_4$ + NaEDTA (2% $Fe^{+2}$) | 2.6 | 35 |
| $FeSO_4$ + PG (2% $Fe^{+2}$) | 2.2 | 6 |
| $FeSO_4$ + PG + NaEDTA (2% $Fe^{+2}$) | 2.6 | 60 |
| Untreated |  | 0 |

EXAMPLE 9

Restoring Dandelion and Dock Infested Lawns with Iron Solutions

This test compared the activity of ferrous sulfate and a solution of ferrous sulfate, citric acid (2%), urea (1%) and EDTA (1.5%). 0.5 m$^2$ areas of turf were sprayed on June 25$^{th}$ and July 7$^{th}$, with observations made on July 13$^{th}$. At the time of the first spraying, grass covered less than 1% of the areas, with dandelions (*Taraxacum officinale*) and dock (*Rumex crispus*) covering the remaining plot areas. The dandelions had leaves 8 to 10 cm long. Iron solutions were applied at 1% $Fe^{+3}$ (179 mM). $Na_4EDTA$ was added to the ferrous sulfate solution at 1.5% (36 mM). The molar level of EDTA is 1/10 that of the iron ions. Citric acid was used at 2% and urea at 1%. The urea is added as a nitrogen fertilizer source to encourage the growth of the grasses.

The plot coverage by various plant species remained unchanged in the untreated areas. The "ferrous sulfate only" treatment reduced the area covered by dock and increased the area covered by turf grasses. However, it did not appear to reduce the area covered by dandelions. The area treated with the ferrous sulfate with added EDTA, citrate and urea showed a dramatic increase in grass coverage, and a reduction in the dandelion and dock coverage. In the area treated with ferrous sulfate with added EDTA, citrate and urea, the dock and dandelions died, leaving bare soil exposed. Grass seed can be re-sown in treated areas 7 days after treatment with no ill effects.

|  | Plot Area Covered (%) By: | | | | Grass Damage |
|---|---|---|---|---|---|
| Observations After 18 days | Grass | Dandelion | Dock | Bare Soil | (0 to 9) |
| Untreated | 1 | 70 | 29 | 0 | 0 |
| $FeSO_4$ (pH 2.4) (1% $Fe^{+2}$) | 20 | 65 | 14 | 1 | 1 |
| $FeSO_4$ (1%) + EDTA, citrate & urea (pH 2.5) (1% Fe) | 45 | 15 | 10 | 30 | 1 |

EXAMPLE 10

Evaluation of FeHEDTA with 0.1% and 0.2% $Fe^{+3}$ on Dandelions

This test investigated using 0.1% (17.9 mM) and 0.2% (35.8 mM) iron, as FeHEDTA, to kill potted dandelions. The solutions contained 10% excess chelating agent.

Small (12 cm diameter) to medium (20 cm diameter) sized, greenhouse-grown dandelions were used. These sizes of dandelions are typically found in lawns. The plants were re-sprayed 7 days after the first spray.

These sizes of dandelions are very susceptible to the FeHEDTA.

| FeHEDTA Conc. As % iron | Dandelion Diameter | Dead Dandelions (#/10) | |
|---|---|---|---|
| Days After Spraying |  | 6 | 7 + 6 |
| FeHEDTA (0.1% Fe) | 12 cm | 2 | 10 |
| FeHEDTA (0.2% Fe) | 12 cm | 8 | 10 |
| FeHEDTA (0.1% Fe) | 16 cm | 1 | 3 |
| FeHEDTA (0.2% Fe) | 16 cm | 3 | 10 |
| FeHEDTA (0.1% Fe) | 20 cm | 0 | 3 |
| FeHEDTA (0.2% Fe) | 20 cm | 1 | 8 |

EXAMPLE 11

Field Test of FeHEDTA, (FeEDDS+Fe MGDA), and Killex to Control Dandelion and Daisy Plants in Lawns.

This test investigated the effect of FeHEDTA and a mixture of FeEDDS and FeMGDA on daisy (*Bellis perennis*), dandelion (*Taraxacum officinale*) and a turf bentgrass (*Agrostis* sp.). The chelating agents were used at one and a half times the molar amount of iron. The FeHEDTA solutions contained 0.2% iron (35.8 mM). The commercially prepared FeHEDTA product from the Monterey Chemical Company (CA, USA) was used as a standard. The (FeEDDS+FeMGDA) solutions contained 0.4% iron (71.6 mM) and the same molar amount of EDDS and MGDA. The solutions were made from NaEDDS (Octaquest E30, Octel) and NaMGDA (Trilon M liquid, BASF, Germany). Ammonium sulfate was added at a concentration of 1%. Killex (Solaris ON, Canada) was diluted and applied as per label instructions of 6 ml/L applied at 200 ml/m$^2$.

The daisy (0.25 m$^2$) and dandelion (0.5 m$^2$) test plots were in different areas of the bentgrass field. The dandelions were large, averaging 30 cm in diameter. The daisy patches were between 10 and 20 cm in diameter. The plants were sprayed weekly 4 times.

The iron treatments were effective at killing the daisy and dandelion plants and did not cause significant grass damage. The only grass damage that was observed was a minor blackening of some of the leaf tips.

| Dandelion Data | Plot Area Covered by Dandelion Plants (%) | | | | Dandelion Necrosis (%) | | | |
|---|---|---|---|---|---|---|---|---|
| Days After Start of Test | 0 | 13 | 21 | 26 | 2 | 9 | 16 | 23 |
| FeHEDTA (0.2% Fe) | 80 | 5 | 10 | 8 | 95 | 98 | 97 | 97 |
| FeHEDTA + NH₄SO₄ (0.2% Fe) | 80 | 5 | 8 | 6 | 90 | 95 | 95 | 95 |
| FeHEDTA (Monterey) (0.2% Fe) | 80 | 15 | 12 | 8 | 85 | 96 | 90 | 92 |
| FeEDDS + FeMGDA (0.4% Fe) | 80 | 10 | 10 | 10 | 80 | 98 | 80 | 95 |
| FeEDDS + FeMGDA + NH₄SO₄ (0.4% Fe) | 75 | 10 | 12 | 10 | 85 | 99 | 85 | 95 |
| Killex | 85 | 85 | 60 | 25 | 0 | 0 | 35 | 65 |
| Water | 85 | 80 | 80 | 90 | 0 | 0 | 0 | 0 |

| Daisy Data | Plot Area Covered by Daisy Plants (%) | | | | Daisy Necrosis (%) | | | |
|---|---|---|---|---|---|---|---|---|
| Days After Start of Test | 0 | 13 | 21 | 30 | 2 | 10 | 16 | 23 |
| FeHEDTA (0.2% Fe) | 60 | 1 | 2 | 0.5 | 20 | 95 | 98 | 98 |
| FeHEDTA + NH₄SO₄ (0.2% Fe) | 35 | 1 | 1 | 1 | 35 | 97 | 98 | 99 |
| FeHEDTA (Monterey) (0.2% Fe) | 40 | 10 | 5 | 0.5 | 35 | 70 | 92 | 90 |
| FeEDDS + FeMGDA (0.4% Fe) | 55 | 5 | 3 | 4 | 35 | 70 | 90 | 80 |
| FeEDDS + FeMGDA + NH₄SO₄ (0.4% Fe) | 45 | 7 | 7 | 2 | 30 | 90 | 92 | 90 |
| Killex | 60 | 25 | 15 | 1 | 0 | 5 | 25 | 45 |
| Water | 50 | 40 | 45 | 45 | 0 | 0 | 0 | 0 |

| Turfgrass Data | Blackening of Bentgrass (Agrostis) Leaf Tips (0 to 9) | | | | | | |
|---|---|---|---|---|---|---|---|
| Days After Start of Test | 1 | 6 | 9 | 16 | 21 | 23 | 30 |
| FeHEDTA (0.2% Fe) | 0 | 0 | 0 | 2 | 0.5 | 0 | 0 |
| FeHEDTA + NH₄SO₄ (0.2% Fe) | 0 | 0 | 0 | 0.5 | 0 | 0 | 0 |
| FeHEDTA (Monterey) (0.2% Fe) | 0 | 0 | 0 | 0.5 | 0 | 0.5 | 0 |
| FeEDDS + FeMGDA (0.4% Fe) | 0.5 | 0.5 | 2 | 3 | 0.5 | 1 | 0 |
| FeEDDS + FeMGDA + NH₄SO₄ (0.4% Fe) | 0 | 1 | 2 | 2 | 0.5 | 1 | 0 |
| Killex | 0 | 0 | 0 | 0 | 0 | 0 | 0 |
| Water | 0 | 0 | 0 | 0 | 0 | 0 | 0 |

EXAMPLE 12

Effect of FeHEDTA on the Chickweed Scarlet Pimpernel and Dandelion

This test evaluated FeHEDTA with 0.15% and 0.2% Fe for controlling the chickweed scarlet pimpernel (*Anagallis arvensis*) and dandelion (*Taraxacum officinale*). The solution contained 1.3 times the molar amount of chelating agent as iron. Field areas of well established chickweed and dandelion (0.5 m²) were sprayed at a rate of 100 ml/m².

FeHEDTA significantly reduced the numbers of dandelions and chickweed plants.

| DANDELION | Dandelion Plants (#/0.5 m²) | | Survival of Dandelion Plants (%) |
|---|---|---|---|
| Days After Spraying | 0 | 7 | day 7/day 0 |
| Untreated | 69 | 69 | 100% |
| FeHEDTA (0.15% Fe) | 57 | 19 | 33 |
| FeHEDTA (0.20% Fe) | 84 | 24 | 29 |

| CHICKWEED | Chickweed Plants (#/0.5 m²) | | Survival of Chickweed Plants (%) |
|---|---|---|---|
| Days After Spraying | 0 | 7 | day 7/day 0 |
| Untreated | 23 | 23 | 100% |
| FeHEDTA (0.15% Fe) | 15 | 8 | 53 |
| FeHEDTA (0.20% Fe) | 25 | 4 | 16 |

EXAMPLE 13

Field Test of FeHEDTA at 0.2% Fe and FeEDDS at 0.4% Fe

This test evaluated FeEDDS (0.4% $Fe^{+3}$) and FeHEDTA (0.2% $Fe^{+3}$) for controlling the weed hairy cat's ear (*Hypochoeris radicata*), also known as "false dandelion", grown in areas of mixed grass and *Hypochoeris*. The iron solutions were sprayed at a rate of 100 ml/m² to 1.0 m² plots. The iron treatments were resprayed after 7 and 14 days. Killex (Solaris ON, Canada) was diluted and applied once as per label instructions of 6 ml/L applied at 200 ml/m².

The Killex treatment did not result in a reduction in the plot area covered by cat's ear, although the plants exhibited severe epinasty symptoms. The grass covered between 15 and 30% of the area over the course of the experiment.

In contrast, the iron treatments eliminated cat's ear from the plots after 3 sprays, even though cat's ear was the predominate weed at the start of the test. The area covered by grass increased 2.5 to 3 fold during the test. None of the treatments caused significant grass phytotoxicity.

| Cat's Ear | Area Covered by Hairy Cat's Ear (%) | | | | | Relative Cat's Ear Area (Start = 100%) | | | | |
|---|---|---|---|---|---|---|---|---|---|---|
| Days After Start of Test | 0 | 6 | 8 | 14 | 18 | 0 | 6 | 8 | 15 | 18 |
| FeHEDTA (0.2% Fe) | 65 | 20 | 20 | 5 | 0 | 100 | 31 | 31 | 8 | 0 |
| FeEDDS (0.4% Fe) | 55 | 20 | 25 | 10 | 0 | 100 | 36 | 45 | 19 | 0 |
| Killex | 55 | 60 | 70 | 70 | 53 | 100 | 109 | 127 | 127 | 96 |
| Untreated | 64 | 55 | 60 | 57 | 70 | 100 | 86 | 94 | 89 | 109 |

-continued

| Grass | Area Covered by Hairy Grass (%) | | | | | Relative Grass Area (Start = 100%) | | | | |
|---|---|---|---|---|---|---|---|---|---|---|
| Days After Start of Test | 0 | 6 | 8 | 15 | 18 | 0 | 6 | 8 | 15 | 18 |
| FeHEDTA (0.2% Fe) | 15 | 47 | 40 | 50 | 46 | 100 | 313 | 267 | 333 | 307 |
| FeEDDS (0.4% Fe) | 20 | 49 | 55 | 50 | 50 | 100 | 245 | 275 | 250 | 250 |
| Killex | 23 | 20 | 15 | 15 | 30 | 100 | 87 | 65 | 65 | 130 |
| Untreated | 15 | 15 | 15 | 10 | 5 | 100 | 100 | 100 | 67 | 33 |

EXAMPLE 14

Field Dandelion Test of FeHEDTA, FeEDTA, FeEDDS, FeMGDA, and 50:50 Mixtures of Chelate Combinations Solutions were made of FeHEDTA (0.2% Fe), FeEDTA (0.2% Fe), FeEDDS (0.4% Fe), and FeMGDA (0.4% Fe). For the combinations, these 4 solutions were mixed together in a 1:1 ratio. The plots (0.25 m$^2$) were sprayed 3 times at weekly intervals at a rate of 0.1 L/m$^2$. The plots contained a mixture of dandelion and hard fescue turfgrass.

All of the iron chelate solutions provided dandelion control that was equal to or better than that provided by Killex. No phytotoxicity was observed on the turfgrass.

| Dandelion | Area Covered by Dandelion (%) | | | | Dandelion Necrosis (%) | | |
|---|---|---|---|---|---|---|---|
| Days After Start of Test | 0 | 6 | 15 | 21 | 33 | 11 | 18 |
| FeHEDTA (0.2% Fe) | 40 | 20 | 8 | 2 | 97 | 95 | 97 |
| FeEDTA (0.2% Fe) | 30 | 10 | 7 | 1 | 90 | 90 | 98 |
| FeEDDS (0.4% Fe) | 25 | 20 | 5 | 1 | 45 | 90 | 70 |
| FeMGDA (0.4% Fe) | 30 | 17 | 12 | 2 | 80 | 85 | 99 |
| FeHEDTA + FeEDTA (0.2% Fe) | 30 | 9 | 5 | 2 | 98 | 90 | 95 |
| FeHEDTA + FeEDDS (0.3% Fe) | 35 | 15 | 12 | 3 | 97 | 80 | 97 |
| FeHEDTA + FeMGDA (0.3% Fe) | 25 | 10 | 5 | 1 | 95 | 98 | 99 |
| FeEDDS + FeMGDA (0.4% Fe) | 30 | 9 | 10 | 3 | 95 | 90 | 98 |
| FeEDDS + FeEDTA (0.3% Fe) | 30 | 20 | 13 | 3 | 80 | 70 | 96 |
| FeEDTA + FeMGDA (0.3% Fe) | 30 | 13 | 6 | 2 | 85 | 85 | 98 |
| Killex | 40 | 30 | 25 | 10 | 15 | 25 | 50 |
| Untreated | 25 | 20 | 60 | 70 | 0 | 0 | 0 |

| Dandelion | Dandelion Count (#/0.25 m$^2$) | | | | Surviving Dandelions (%) | | |
|---|---|---|---|---|---|---|---|
| Days After Start of Test | 0 | 6 | 13 | 21 | 6 | 13 | 21 |
| FeHEDTA (0.2% Fe) | 63 | 60 | 40 | 26 | 95 | 63 | 41 |
| FeEDTA (0.2% Fe) | 56 | 33 | 20 | 19 | 59 | 36 | 34 |
| FeEDDS (0.4% Fe) | 53 | 40 | 19 | 16 | 75 | 36 | 30 |
| FeMGDA (0.4% Fe) | 72 | 71 | 43 | 19 | 99 | 60 | 26 |
| FeHEDTA + FeEDTA (0.2% Fe) | 58 | 37 | 27 | 18 | 64 | 47 | 31 |
| FeHEDTA + FeEDDS (0.3% Fe) | 67 | 57 | 53 | 21 | 85 | 79 | 31 |
| FeHEDTA + FeMGDA (0.3% Fe) | 45 | 28 | 19 | 13 | 62 | 42 | 29 |
| FeEDDS + FeMGDA (0.4% Fe) | 59 | 51 | 42 | 20 | 86 | 71 | 34 |
| FeEDDS + FeEDTA (0.3% Fe) | 55 | 55 | 47 | 23 | 100 | 85 | 42 |
| FeEDTA + FeMGDA (0.3% Fe) | 62 | 41 | 32 | 17 | 66 | 52 | 27 |
| Killex | 55 | 50 | 38 | 33 | 91 | 69 | 60 |
| Untreated | 49 | 51 | 49 | 53 | 100 | 100 | 100 |

EXAMPLE 15

Greenhouse Dandelion Damage of FeEDDS with Various Additives

This test investigated combinations of various chelating agents with FeEDDS. All of the solutions contained 0.4% iron (71.6 mM). The chelating agents were made as sodium salts and added to a solution of FeEDDS. The solutions were sprayed onto greenhouse-grown dandelions at a rate of 100 ml/m². The test was resprayed after 7 days.

All of the solutions were effective at controlling dandelions.

| Dandelion | Dandelion Necrosis (%) | | Dead Dandelion (#/20) | |
|---|---|---|---|---|
| Days After Start of Test | 1 | 10 | 7 | 10 |
| FeEDDS 0.4% Fe (A) | 67 | 96 | 6 | 10 |
| (A) + citric 2% (0.4% Fe) | 89 | 98 | 5 | 14 |
| (A) + gluconic 2% (0.4% Fe) | 87 | 98 | 7 | 11 |
| (A) + lactic 2% (0.4% Fe) | 84 | 98 | 3 | 12 |
| (A) + malonic 2% (0.4% Fe) | 90 | 99 | 10 | 18 |
| (A) + malic 2% (0.4% Fe) | 93 | 98 | 11 | 17 |
| (A) + glycine 2% (0.4% Fe) | 84 | 97 | 7 | 18 |
| Untreated | 0 | 0 | 0 | 0 |

EXAMPLE 16

Comparison of Different Salts of EDTA on Greenhouse Dandelion Mortality

This test investigated various metal chelates. All chelate solutions contained 0.4% metal ions with 10% excess chelator, and were adjusted to pH 7. For the combinations, these 4 solutions were mixed together in a 1:1 ratio. The solutions were sprayed onto greenhouse grown dandelions at a rate of 100 ml/m². The test was re-sprayed after 7 days.

FeEDTA is a better herbicide than Al EDTA, Cu EDTA and ZnEDTA. Also 1 to 1 mixtures of Fe EDTA with other metal chelates caused the same damage as FeEDTA.

| Dandelion | Dead Dandelion (#/20) | |
|---|---|---|
| Days After Start of Test | 7 | 10 |
| Fe EDTA (0.4% Fe) | 10 | 17 |
| Al EDTA (0.4% Al) | 0 | 0 |
| Cu EDTA (0.4% Cu) | 0 | 4 |
| Zn EDTA (0.4% Zn) | 0 | 0 |
| (Fe + Al) EDTA (0.2% Fe + 0.2% Al) | 8 | 17 |
| (Fe + Cu) EDTA (0.2% Fe + 0.2% Cu) | 3 | 16 |
| (Fe + Zn) EDTA (0.2% Fe + 0.2% Zn) | 0 | 14 |
| FeCl₃ (0.4% Fe) | 0 | 0 |
| Untreated | 0 | 0 |

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for selectively treating undesired vegetation, comprising the steps of:
   providing a herbicidal composition of a transition metal complex formed from a transition metal component selected from the group consisting iron, copper, zinc, manganese, and mixtures thereof, and
   a chelating agent selected from the group consisting of an aminopolycarboxylate, an amino acid, and a salicylate; and
   contacting vegetation with a herbicidally effective amount of the composition, such that the vegetation is selectively controlled.

2. The method of claim 1, wherein the transition metal component is present within the composition at a molar amount equal to or greater than an amount of chelating agent.

3. The method of claim 2, wherein a molar ratio of the transition metal component to the chelating agent is in the range of about 1.0:0.05 to 1.0:1.0.

4. The method of claim 2, wherein a molar ratio of the transition metal component to the chelating agent is in the range of about 1.0:0.1 to 1.0:1.0.

5. The method of claim 1, wherein the chelating agent is selected from the group consisting of diamino cyclohexane tetraacetic acid, ethylenediaminedisuccinic acid, ethylenediaminetetraacetic acid, ethanoldiglycine, hydroxyethylenediaminetriacetic acetic acid, methylglycinediacetic acid, glutamicaciddiacetic acid, trans-1,2-diaminocyclohexane-N,N,N',N'tetraacetic acid, diethylenetriaminepentaacetic acid, ethylenediaminetetraacetic acid, iminodisuccinic acid, their salts, and combinations thereof.

6. The method of claim 1, wherein the chelating agent is present within the composition at a molar amount equal to or greater than an amount of the transition metal.

7. The method of claim 6, wherein a molar ratio of the transition metal to the chelating agent is in the range of about 0.05:1.0 to 1.0:1.0.

8. The method of claim 6, wherein a molar ratio of the transition metal to the chelating agent is in the range of about 0.1:1.0 to 1.0:1.0.

9. The method of claim 6, wherein the chelating agent is selected from the group consisting of diamino cyclohexane tetraacetic acid, ethylenediaminedisuccinic acid, ethylenediaminetetraacetic acid, ethanoldiglycine, hydroxyethylenediaminetriacetic acid methylglycinediacetic acid, glutamicaciddiacetic acid, their salts, and combinations thereof.

10. The method of claim 1, further comprising a third component selected from the group consisting of growth regulators, fertilizers, herbicides, thickening agents, humectants, antioxidants, surfactants, stabilizing agents, wetting agents, herbicide synergists, sequestrants, solvents, dyes, and combinations thereof.

11. A method for selectively treating undesired vegetation, comprising the steps of:
    providing a herbicidal composition having an iron ion and a chelating agent selected from the group consisting of diamino cyclohexane tetraacetic acid, ethylenediaminesuccinic acid, ethylenediaminetetraacetic acid, ethanoldiglycine, hydroxyethylenediaminetriacetic acid, methylglycinediacetic acid, glutamicaciddiacetic acid, trans-1,2-diaminocyclohexane-N,N,N', N'tetraacetic acid, diethylenetriaminepentaacetic acid, ethylenediaminetetraacetic acid, iminodisuccinic acid, and combinations thereof; and contacting vegetation with a herbicidally effective amount of the composition, such that the vegetation is selectively controlled.

12. The method of claim 11, further comprising a third component selected from the group consisting of growth regulators, fertilizers, herbicides, thickening agents, humectants, antioxidants, surfactants, stabilizing agents, wetting agents, herbicide synergists, sequestrants, solvents, dyes, and combinations thereof.

13. A method for selectively treating undesired vegetation, comprising the steps of:

providing a herbicidal composition having a transition metal chelate formed from a transition metal selected from the group consisting of iron, copper, zinc, manganese, and mixtures thereof and a chelating agent selected from the group consisting of diamino cyclohexane tetraacetic acid, ethylenediaminedisuccinic acid, ethylenediaminetetraacetic acid, ethanoldiglycine, hydroxyethylenediaminetriacetic acid, methylglycinediacetic acid, glutamicaciddiacetic acid, trans-1,2-diaminocyclohexane-N,N,N', N'tetraacetic acid, diethylenetriaminepentaacetic acid, ethylenediaminetetraacetic acid, iminodisuccinic acid, their salts, and combinations thereof; and contacting vegetation with a herbicidally effective amount of the composition, such that the vegetation is selectively controlled.

14. The method of claim 13, wherein the transition metal is present within the composition at a concentration of about 0.1 to 2.0% by weight.

15. A method for selectively treating undesired vegetation, comprising the steps of:

providing a herbicidal composition of an iron chelate complex of a chelating agent selected from the group consisting of an aminopolycarboxylate, an amino acid, and a salicylate; and contacting vegetation with a herbicidally effective amount of the composition, such that the vegetation is selectively controlled.

* * * * *